United States Patent [19]

Duncan

[11] Patent Number: 4,548,202
[45] Date of Patent: Oct. 22, 1985

[54] MESH TISSUE FASTENERS

[75] Inventor: Robert B. Duncan, Bridgewater, N.J.

[73] Assignee: Ethicon, Inc., Somerville, N.J.

[21] Appl. No.: 506,142

[22] Filed: Jun. 20, 1983

[51] Int. Cl.⁴ ............................................. A61B 17/04
[52] U.S. Cl. ............................ 128/334 C; 227/DIG. 1
[58] Field of Search ........... 128/346, 337, 335, 334 R, 128/334 C, 330, 325, 326, 92 B; 3/1; 227/DIG. 1, 15–18, 77; 411/469, 451, 360, 501, 506, 362–364, 455–457; 24/543, 518, 614, 623, 703, 297, 150 FP, 16 PB, 697, 580, 581, 584, 453, 30.5 P, 537, 515, 513, 503, 94–96

[56] References Cited

U.S. PATENT DOCUMENTS

| | | | |
|---|---|---|---|
| Re. 27,391 | 6/1972 | Merser ........................ | 24/150 FP X |
| 306,479 | 10/1884 | Goddard ..................... | 24/95 |
| 389,660 | 9/1888 | Mandel et al. ................ | 411/457 X |
| 579,831 | 3/1897 | Ketchum ..................... | 24/95 |
| 1,988,233 | 1/1935 | Berendt ....................... | 24/95 |
| 2,794,981 | 6/1957 | Brayton ....................... | 227/15 |
| 2,881,762 | 4/1959 | Lowrie ........................ | 128/337 |
| 2,897,561 | 8/1959 | Megibow ..................... | 24/95 |
| 2,900,696 | 8/1959 | Bacon ......................... | 24/614 X |
| 3,009,852 | 11/1961 | Gruner ........................ | 128/330 X |
| 3,166,072 | 1/1965 | Sullivan ....................... | 128/346 X |
| 3,210,820 | 10/1965 | Humiston ..................... | 24/584 X |
| 3,326,217 | 6/1967 | Kerr ............................ | 227/DIG. 1 C X |
| 3,357,296 | 12/1967 | Lefever ....................... | 128/334 C X |
| 3,494,006 | 2/1970 | Brumlik ....................... | 411/456 X |
| 3,570,497 | 3/1971 | Lemole ........................ | 128/335.5 |
| 3,577,601 | 5/1971 | Mariani et al. ............... | 24/16 |
| 3,683,927 | 8/1972 | Noiles ......................... | 128/326 X |
| 3,744,495 | 7/1973 | Johnson ...................... | 128/330 |
| 3,802,438 | 4/1974 | Wolvek ....................... | 128/335 |
| 3,857,396 | 12/1974 | Hardwick ..................... | 128/335 |
| 3,875,648 | 4/1975 | Bone ........................... | 227/19 X |
| 3,981,051 | 9/1976 | Brumlik ....................... | 411/456 X |
| 4,006,747 | 2/1977 | Kronenthal et al. .......... | 128/337 X |
| 4,038,725 | 8/1977 | Keefe .......................... | 24/150 FP |
| 4,060,089 | 11/1977 | Noiles ......................... | 128/337 X |
| 4,235,238 | 11/1980 | Ogiu et al. ................... | 128/335 X |
| 4,259,959 | 4/1981 | Walker ........................ | 128/337 |
| 4,294,255 | 10/1981 | Geroc ......................... | 128/334 C |
| 4,326,531 | 4/1982 | Shimonaka .................. | 128/326 |
| 4,400,833 | 8/1983 | Kurland ....................... | 3/1 |
| 4,402,445 | 9/1983 | Green ......................... | 128/334 R X |
| 4,454,875 | 6/1984 | Pratt et al. ................... | 128/92 B |

FOREIGN PATENT DOCUMENTS

| | | | |
|---|---|---|---|
| 1097171 | 3/1981 | Canada ....................... | 128/330 |
| 1385691 | 12/1964 | France ........................ | 40/300 |
| WO83/01190 | 4/1983 | PCT Int'l Appl. ............ | 227/DIG. 1 |
| 82738 | 10/1919 | Switzerland ................. | 128/330 |
| 972731 | 10/1964 | United Kingdom .......... | 128/346 |

Primary Examiner—Michael H. Thaler
Attorney, Agent, or Firm—Robert L. Minier

[57] ABSTRACT

Various fasteners are provided to hold together portions of mammalian tissue. The fasteners include fastening members with spaced-apart legs adapted to be passed through the tissue portions. One embodiment of the fastener has a mesh-like receiver around each leg for engaging the legs of another identical fastening member inserted from an opposite side of the tissue portions. In other embodiments, the receiver is a separate element and is applied to a side of the tissue portions opposite the fastening member to engage the legs of the fastening member. The receiver may have a variety of forms. A number of structures are disclosed for effecting engagement of the fastening member legs with the receiver.

2 Claims, 14 Drawing Figures

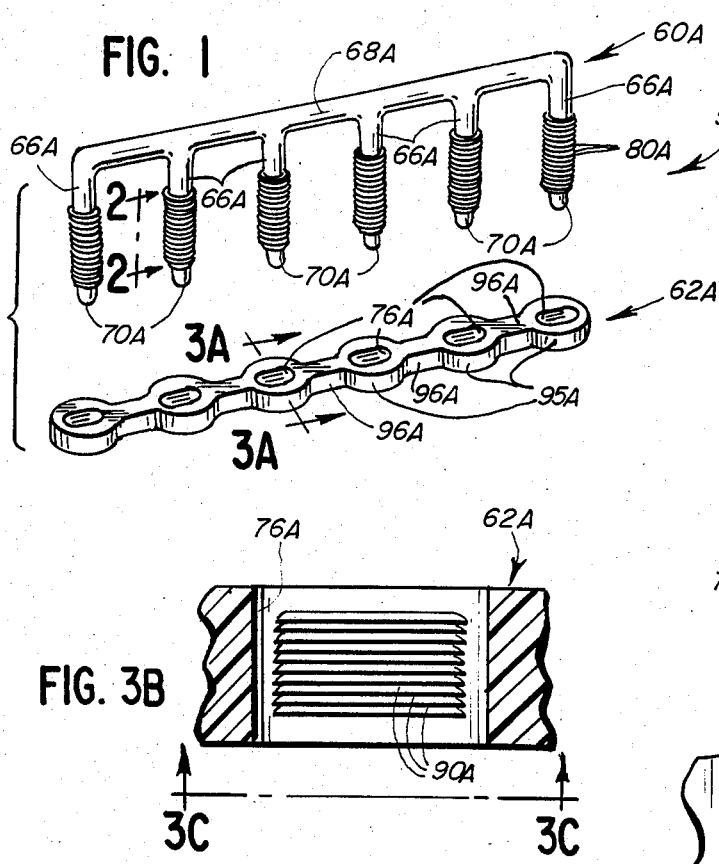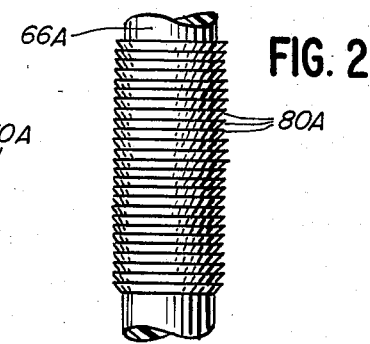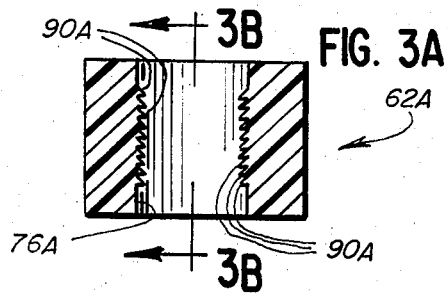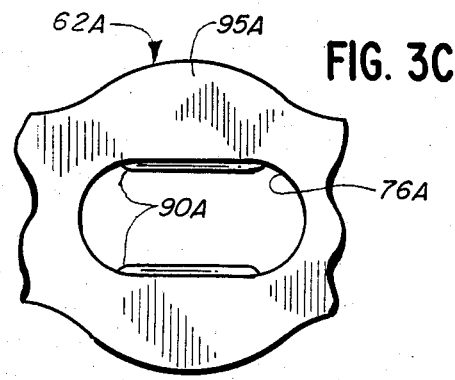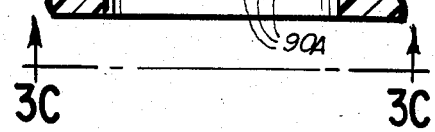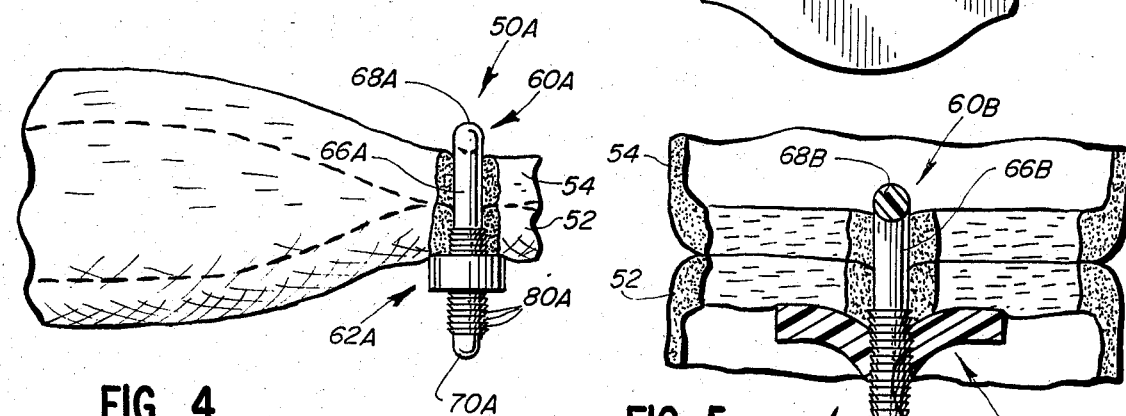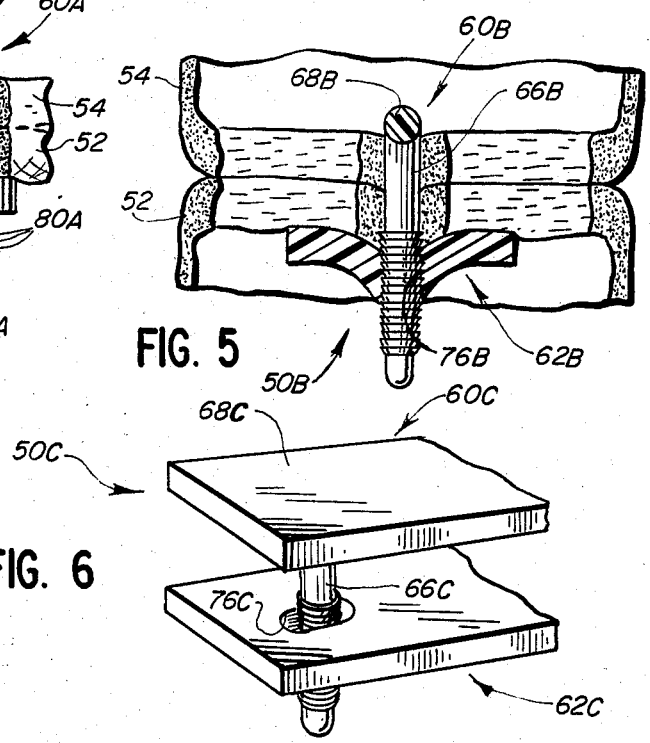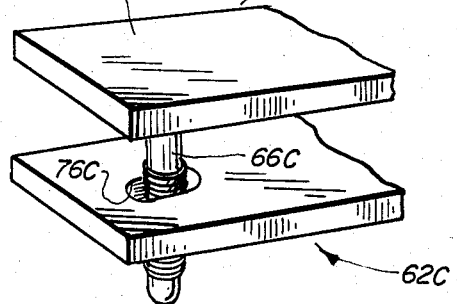

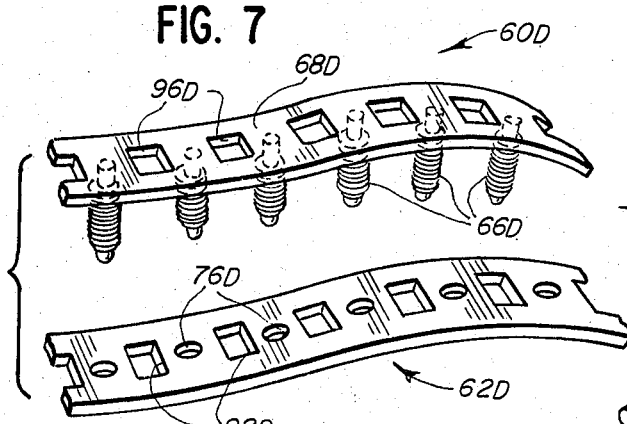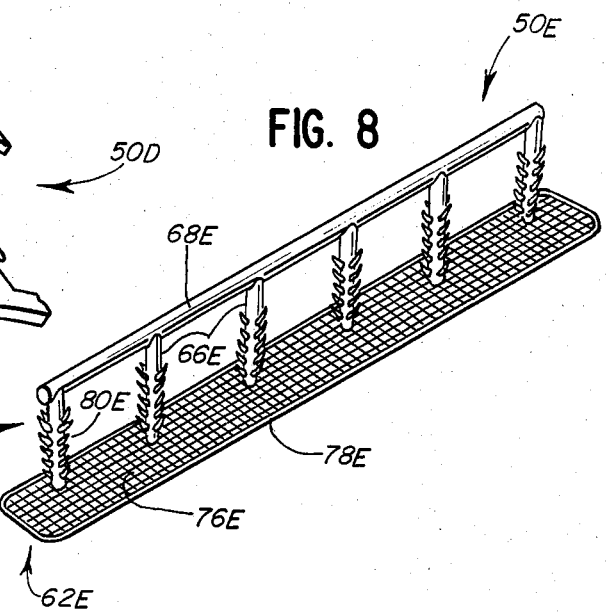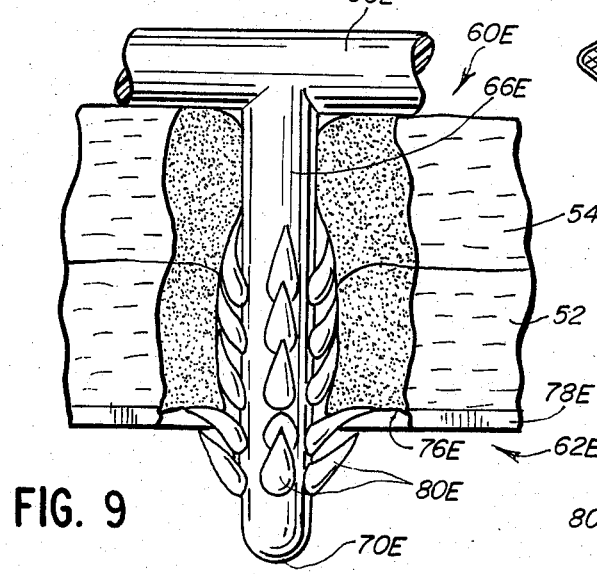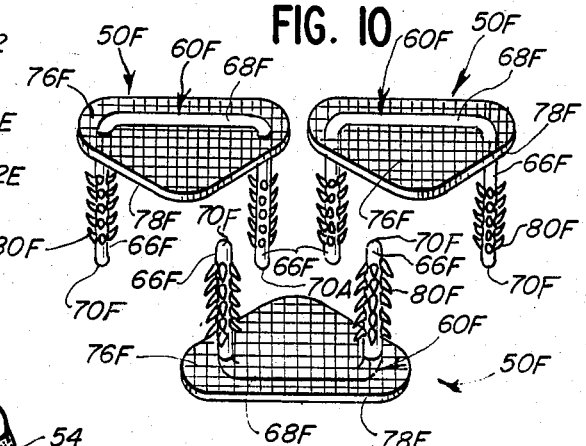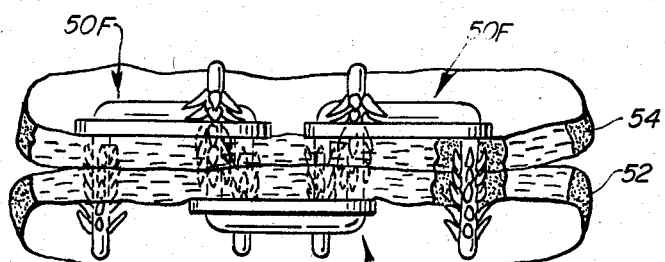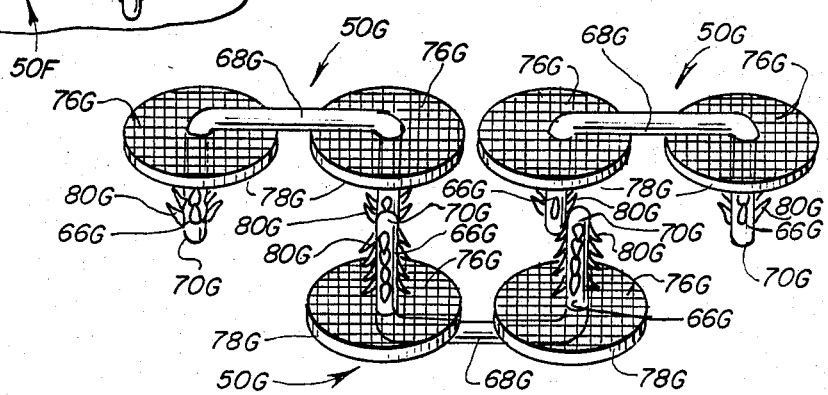

MESH TISSUE FASTENERS

DESCRIPTION

Technical Field

This invention relates, in general, to the fastening together of portions of tissue in surgical procedures.

BACKGROUND OF THE INVENTION

In various surgical procedures, fasteners in the form of staples or the like are employed for holding tissue portions together to facilitate healing of a wound or incision. For example, a locking staple, having a tongue and groove structure by which the staple is locked, is disclosed in U.S. Pat. No. 2,881,762. A metal staple especially adapted for ligating blood vessels is disclosed in U.S. Pat. No. 3,079,608. International patent application No. PCT/SU79/00049 discloses a variety of fastening devices and instruments for performing circular anastomoses on the large intestine. The aforementioned disclosures serve to illustrate the wide variety of tissue fastening devices and techniques that may be employed in general and/or specific surgical situations.

One common type of fastening device for joining or holding together soft tissue portions is the generally "U"-shaped staple which is typically fabricated from a suitable metal. Such staples, although generally described as having two legs joined to define a "U"-shape when unclinched, may also be regarded as having a configuration of an "open" loop when unclinched. The legs need not necessarily be parallel but are typically adapted for penetrating the tissue portions and for receiving between them some of the tissue material.

Other examples of U-shaped or open loop staples, as well as of methods and instruments for applying such staples to tissue, are disclosed in U.S. Pat. Nos. 3,252,643, 3,482,428, 3,692,224, 3,790,057, 3,795,034, 3,889,683, 4,198,982, 4,316,468, and 4,319,576.

Other tissue fastening devices have been proposed and differ from staples per se in that these other devices may have a plurality of components and do not have to be clinched in the manner used to set a staple. One such device is disclosed in U.S. Pat. No. 4,060,089 and includes a fastener strip provided with a plurality of longitudinally spaced, parallel prongs which are adapted to penetrate two overlapped tissue portions from one side so that the distal ends of the prongs project from the other side of the tissue portions.

The fastener device further includes a retainer strip which is adapted to be placed on the other side of the tissue portions opposite the fastener strip to engage the ends of the projecting fastener strip prongs and thus secure the tissue portions tightly between the fastener strip and the retainer strip. The retainer strip defines frustoconical openings for receiving the fastener strip prongs which each include a plurality of spaced-apart, frustoconical engaging members for engaging the retainer strip at a desired position relative to the prongs. This provides for the capability of adjusting the distance between the fastener strip and the retainer strip. Such a fastening device may be fabricated from a biodegradable or absorbable material.

Yet another tissue fastening device having a plurality of components is disclosed in co-pending commonly assigned U.S. patent application Ser. No. 349,433, filed Mar. 18, 1982. The fasteners disclosed in that application are made from various polymeric materials and the legs of the U-shaped staple portion of the fastener have a taper to improve the penetration of the staple into tissue.

Although many of the above-discussed types of tissue fastening devices and techniques are satisfactory in various applications, there is a need to provide an improved fastening device, especially one completely fabricated from absorbable materials.

Also, it would be desirable to provide an improved fastening device fabricated from absorbable materials that can provide primary approximation of the tissue edges to insure that the tissue edges are in continuous contact. Further, such an improved fastener should provide a desired amount of hemostatic compression to minimize bleeding, but allow some collateral blood circulation to the wound or incision edges of the tissue to promote healing. In addition, such an improved fastener should have the capability to accommodate varying tissue thicknesses and should leave as little tissue cuff or margin as possible in effecting the joining of the tissue.

Further, it would be beneficial if such an improved fastener had a configuration that, consistent with other design considerations, would enable the fastener to be fabricated with (1) as small a size as possible to minimize dosage and (2) with a minimum of sharp edges or protrusions. Also, another desirable feature of such an improved fastener would be a fastener configuration that did not form, or contribute to the formation of, pockets of infection in the tissue.

Further, such an improved fastener would desirably provide the surgeon with the capability for readjusting the compression after initial application.

Such an improved fastener should have the capability for maintaining the tissue portions in approximation and compression for a minimum of 21 days in vivo. Also, such a fastener should desirably be easily adjustable to the length of the two tissue portions being joined so that a single fastener can be used, rather than a plurality of shorter fasteners. Further, the fastener should desirably produce a well-distributed clamping force on the tissue portions.

It would also be advantageous to provide such a fastener with a design that would facilitate its application to the tissue portions with a simple yet effective method. It would additionally be desirable if the improved fastener could readily accommodate application by means of an appropriately designed instrument.

SUMMARY OF THE INVENTION

Improved fasteners are provided to hold together portions of mammalian tissue, such as are defined by a wound or incision, to facilitate healing of the wound or incision.

One fastener includes a fastening member that has a plurality of spaced-apart, serrated legs adapted to penetrate the tissue portions and that has an elongate clamping member connecting the legs. The fastener further includes an elongate receiver adapted to be disposed against a tissue portion opposite the fastening member for receiving the fastening member legs. The receiver defines apertures each having a plurality of serrations for cooperating with the serrations on the fastening member legs to inhibit relative movement of the receiver and fastening member at least in the disengaging directions.

In one form of the fastener, the clamping member and receiver are generally rigid. In another form of the fastener, both the clamping member and receiver are flexible strips which can generally conform to the surface contour of one of the tissue portions. The fastening member legs and receiver have suitable engaging means which may include serrations or other cooperating structures.

In a modification of this flexible component fastener, the flexible clamping member strip has regions defined between legs where one or more shorter lengths of the clamping strip may be separated from the longer clamping strip. The receiver strip also defines regions between leg receiving means where one or more shorter lengths of the receiver strip may be separated.

The above-described flexible, severable forms of the fastener components may be applied to the tissue according to a novel method. Specifically, a shorter length of a fastening member clamping strip may be separated from the originally provided longer fastening member clamping strip. A shorter length of the receiver strip may be separated from the longer length of the receiver strip originally provided. The shorter length of the clamping strip is disposed against one tissue portion. The shorter length of the receiver strip is disposed against the other of the tissue portions while conforming the shorter length receiver strip to the surface contour of the other tissue portion.

Then the legs of the shorter length of the fastening member are inserted through the tissue portions and through the shorter length of the receiver strip to conform the clamping strip portion of the shorter length of the fastening member to the surface contour of the one tissue portion with the legs of the fastening member engaged with the shorter length of the receiver strip.

The above-described method may be used with a flexible fastener wherein the fastening member and receiver are not designed to be severable. In such a case, the fastener is provided in various specific sizes and the user initially selects the appropriate size fastener rather than sever a longer fastener.

The above-described method may be used for applying an elongate, flexible fastening member clamping strip and an elongate, flexible receiver to conform to the surface contour of the tissue portions even if the fastening member legs are received in receiver structures other than those having serrated apertures. The method may be effectively employed with fastening members and receivers having other forms of engaging structures for holding the legs of the fastening member within the receiver.

In still another form of the fastener, a fastening member is provided with a clamping member connecting a plurality of legs that each have a plurality of barbs angled rearwardly away from the leg distal end. The fastener also includes a receiver in the form of a mesh of flexible filaments adapted to receive the fastening member legs after the legs have been inserted through the tissue portions with the barbs engaging the both mesh and one of the tissue portions so as to inhibit relative movement of the receiver and fastening member at least in the disengaging directions. According to the method for applying this type of fastener, the receiver is disposed against one of the tissue portions and the fastening member is disposed against the other of the two tissue portions so that the legs of the fastening member penetrate the tissue portions and the receiver mesh.

In yet another form of the fastener, at least first and second identical fastening members are provided. Each fastening member comprises a plurality of spaced-apart legs with distal ends and each fastening member also includes a mesh of flexible filaments extending around each of the legs. According to a method for applying the fastener, the first fastening member is disposed against one of the tissue portions and the second fastening member is disposed against the other of the tissue portions. The tissue portions are penetrated by the legs of each fastening member so that the legs of each fastening member engage the mesh of the other fastening member to prevent disengagement and to hold the tissue portions together.

Numerous other features of various embodiments of the novel tissue fasteners and application methods will be apparent from the following detailed description and accompanying drawings.

BRIEF DESCRIPTION OF THE DRAWINGS

In the accompanying drawings forming part of the specification, and in which like numerals are employed to desginate like parts throughout the same, FIG. 1 is a perspective view of a fastening member and receiver which together constitute a first embodiment of the fastener of the present invention;

FIG. 2 is a greatly enlarged, fragmentary, side view of one of the fastening member legs taken generally along the plane 2—2 in FIG. 1;

FIG. 3A is a greatly enlarged, cross-sectional view of the receiver taken generally along the plane 3A—3A in FIG. 1;

FIG. 3B is a fragmentary, cross-sectional view taken generally along the plane 3B—3B in FIG. 3A;

FIG. 3C is a fragmentary, bottom view taken generally along the plane 3C—3C in FIG. 3B;

FIG. 4 is a view of the fastener of FIGS. 1–3C shown applied to tissue portions with part of the tissue portions cut away to better illustrate interior detail;

FIG. 5 is a fragmentary, cross-sectional view of a second embodiment of a fastener shown holding together two portions of tissue;

FIG. 6 is a fragmentary, perspective view of a third embodiment of a fastener shown assembled in the absence of tissue;

FIG. 7 is a perspective view of a fourth embodiment of a fastener;

FIG. 8 is a perspective view of a fifth embodiment of a fastener;

FIG. 9 is a greatly enlarged, fragmentary view of the fastener of FIG. 8 shown applied to tissue portions to hold together tissue portions with parts of the tissue portions cut away to better illustrate interior detail;

FIG. 10 is a perspective view of three fasteners that each have the form of a sixth embodiment of a fastener;

FIG. 11 is a view of the fasteners of FIG. 10 shown applied to hold together two tissue portions with parts of the tissue portions cut away to better illustrate interior detail; and FIG. 12 is a perspective view of three fasteners that each have the form of a seventh embodiment of a fastener.

DESCRIPTION OF THE PREFERRED EMBODIMENTS

This invention may be used in many different forms. The specification and accompanying drawings disclose only a few specific forms as an example of the use of the invention. The precise shapes and sizes of the components herein described are not essential to the invention unless otherwise indicated. The invention is not intended to be limited to the embodiments of the method and article illustrated, and the scope of the invention will be pointed out in the appended claims.

FIRST EMBODIMENT OF THE FASTENER

A first embodiment of the fastener is illustrated in FIGS. 1–4 and is designated generally therein by reference numeral 50A.

The fastener 50A is illustrated in FIG. 4 in the fully assembled, "set" configuration wherein it is shown holding together two portions 52 and 54 of mammalian tissue, such as are defined by a wound or incision in an organ, to facilitate healing of the wound or incision.

The fastener 50A includes two components, a fastening member 60A and a receiver 62A, which are initially separated as illustrated in FIG. 1 and which are adapted to cooperate to compress or hold between them the tissue portions as illustrated in FIG. 4.

As is best illustrated in FIG. 1, the fastening member 60A includes (1) a plurality of spaced-apart legs 66A adapted to penetrate the tissue portions and (2) an elongate clamping member 68A which connects the legs 66A and which is adapted to lie substantially against one of the tissue portions (e.g., tissue portion 54 in FIG. 4). The legs 66A of the fastening member 60A are generally parallel to each other and are generally perpendicular to the clamping member 68A. Preferably, each leg 66A has a solid, generally cylindrical configuration with a conical distal end 70A to facilitate or aid in the penetration of the tissue portions. The clamping member 68A may be cylindrical (as illustrated) or may have any other suitable shape (such as that of a regular parallelpiped, for example).

The fastener 50A is provided with unique means for effecting engagement between the fastening member 60A and the receiver 62A and for holding the fastening member 60A and receiver 62A in a desired relationship to compress between them the two tissue portions 54 and 52 as illustrated in FIG. 4. To this end, as best illustrated in FIGS. 1 and 2, each leg 66A of the fastening member 60A defines on its exterior along at least a portion of its length a plurality of small teeth or serrations 80A.

Further, as best illustrated in FIG. 4, the receiver 62A is adapted to be disposed against the other of the tissue portions opposite the fastening member 60A. The receiver 62A defines means for receiving the fastening member legs and means for being engaged by the fastening member legs after the legs have been inserted through the tissue portions. The means for receiving the fastening member legs includes, in this embodiment, a plurality of spaced-apart apertures 76A as illustrated in FIG. 1. The apertures 76A may have the form of elongate or oval bores as illustrated.

The receiver 62A defines in each aperture 76A a plurality of small teeth or serrations 90A for cooperating with the serrations 80A on the fastening member legs so as to inhibit relative movement of the receiver 62A and of the fastening member 60A in the disengaging directions (in the directions tending to pull the components apart from the set position illustrated in FIG. 4). The receiver aperture serrations 90A are functional in one of two directions relative to the leg serrations 80A for a given orientation of the receiver relative to the fastening member. In this respect, as best illustrated in FIGS. 2 and 3A, each receiver serration 90A is defined by a first retaining surface generally normal to the wall of the aperture 76A and by a second camming surface slanting at an angle relative to the first retaining surface.

Each fastening member leg serration 80A has the form of a small frustoconical structure with a first surface generally normal to the cylindrical exterior surface of the legs 66A and with a second surface slanting at an angle relative to the first surface. By orienting the serration slanting surfaces on the leg in a direction opposite to the slanting surfaces of the serrations on the receiver, the legs 66A may be inserted into the receiver 62A so that the serration slanting surfaces accommodate relative movement in the direction of the insertion. However, the normal surfaces of the serrations of the fastening member leg 66A and of the receiver 62A engage to prevent withdrawal of the leg 66A from the receiver 62A. This action is enhanced by providing a somewhat resilient serration structure.

Also, as best illustrated in FIG. 3A, the width of each receiver aperture 76A between the serrations 90A may be slightly less than the diameter of the frustoconical serrations 80A on the fastening member leg 66A. This will ensure a temporary deflection or deformation of the serrations 80A as the leg 66A is inserted into a aperture 76A of the receiver 62A. When the leg 66A has been inserted a desired amount, the serrations 80A will tend to spring outwardly of the original, undeformed orientation so as to fully engage the serrations 90A of the receiver and prevent withdrawal of the fastening member 60A from the receiver 62A.

As best illustrated in FIGS. 1 and 3C, the receiver 62A may have an enlarged portion 95A adjacent or surrounding each aperture 76A. This allows the receiver 62A to be fabricated with a narrow connecting portion 96A (FIG. 1). The narrow connecting portion 96A may have a width considerably less than the width of the receiver portion 95A around each aperture 76A. Indeed, if desired, each portion 96A may have a width less than the width of the aperture 76A. The provision of the enlarged portion 95A adjacent or around each aperture 76A provides sufficient material to define each aperture 76A and to provide the necessary structural integrity while permitting the use of the very narrow portions 96A to conserve material.

The fastening member 60A and receiver 62A may be formed from suitable materials, such as thermoplastic polymer materials that are absorbable by mammalian tissue. For example, the fastening member and receiver may be molded from absorbable polymers or copolymers of poly-dioxanone, lactide, glycolide and the like. These components may also be molded from a combination of such materials.

The fastener 50A is used to join the tissue portions 52 and 54 (FIG. 4) in a novel manner. Specifically, the tissue portions 52 and 54 are first approximated in surface-to-surface relationship as best illustrated in FIG. 4. Then the fastening member 60A is positioned on one side of the tissue portions with the legs 66A oriented at an appropriate angle to penetrate the tissue portions. The receiver 62A is held on the other side of the tissue portions opposite the fastening member 60A and generally in alignment with the fastening member legs 66A. Specifically, the apertures 76A are aligned with the fastening member legs 66A.

Next, relative movement between the fastening member 60A and the receiver 62A is effected to urge the fastening member and the receiver closer together to cause the fastening member legs 66A to penetrate the tissue portions 52 and 54 and to locate at least portions of the fastening member legs 66A within the receiver 62A. The relative movement between the fastening member 60A and the receiver 62A is terminated when the clamping member 68A is at a desired distance from the receiver 62A to secure the tissue portions together. Preferably, this movement is terminated after the tissue portions have been compressed together a desired amount.

At this point, the distal ends of the fastening member legs 66A will typically protrude from the receiver 62A opposite the side of the receiver that is contacting one of the tissue portions. If desired, the protruding ends of the legs 66A may be severed flush with the bottom of the receiver 62A by a suitable means. Preferably, during the step of severing the protruding portions of the fastening member legs 66A, the protruding portions of the fastening member legs are surrounded with a suitable container for catching the leg protruding portions after they are severed so as to prevent the severed portions of the legs from falling into the surrounding tissue or body cavity.

The above-described method for applying the fastener 50A to the tissue portions 52 and 54 may be effected with a suitable instrument (not illustrated) specifically designed for holding the fastening member 60A and receiver 62A and for driving the fastening member 60A through the tissue portions and into engagement with the receiver 62A. Such an instrument may include a pair of pivotally mounted jaws with one of the jaws adapted for holding the receiver 62A on one side of the tissue portions and with the other of the jaws adapted for holding the fastening member 60A on the other side of the tissue portions. A suitable driving member may be provided as part of the instrument for driving the fastening member 60A out of its holding jaw, into the tissue portions, and finally into engagement with the receiver 62A.

The instrument may include a suitable mechanism for severing the protruding portions of the fastening member legs 66A after the fastening member 60A and receiver 62A have been locked together with the tissue portions under the desired amount of compression. It is to be realized that such an instrument might be preferably provided with means for applying a plurality of such fasteners simultaneously or with means for accommodating longer or shorter fasteners.

SECOND EMBODIMENT OF THE FASTENER

The second embodiment of the fastener is illustrated in FIG. 5 and is designated generally therein by reference numeral 50B. The fastener 50B includes a fastening member 60B and a receiver 62B.

The fastener 50B is similar to the first embodiment of the fastener 50A described above with reference to FIGS. 1-4. The elements of the second embodiment of the fastener 50B that are identical or functionally analogous to those of the first embodiment of the fastener 50A are designated by reference numerals identical to those used for the first embodiment with the exception that the second embodiment reference numerals are followed by the upper case letter B whereas the first embodiment reference numerals are followed by the upper case letter A.

The fastening member 60B is identical to the fastening member 60A of the first embodiment of the fastener 50A described above with reference to FIG. 1 and has legs 66B joined by a clamping member 68B.

The receiver 62B is somewhat similar to the receiver 62A of the first embodiment of the fastener 50A described above with reference to FIG. 1. However, rather than being a completely rigid member like receiver 62A, the receiver 62B has at least a central portion around each aperture 76B that is flexible. This feature can be provided by making the receiver 62B somewhat thinner than the receiver 62A.

In any case, the apertures 76B of the receiver 62B are provided with serrations and the legs 66B of the fastening member 60B are also provided with serrations. The serration structure is preferably identical to that described above with reference to the first embodiment of the fastener 50A. Thus, when the fastener is applied to the tissue, the serrations on the fastening member legs 66B are engaged by the serrations on the receiver 62B.

Each aperture 76B of the receiver 62B may be elongate or oval as are the apertures 76A of the first embodiment of the fastener 50A discussed above. Also, the width of each aperture 76B is preferably slightly less than the diameter of each of the legs 66B of the fastening member 60B.

Owing to the flexible nature of at least the region of the receiver 62B around each aperture 76B, the flexible regions are forced outwardly some amount when the fastening member 60B is inserted through the tissue portions and into the receiver 62B as illustrated in FIG. 5. The outward deflection of the flexible regions of the receiver 62B facilitate reception of the fastening member legs 66B in the receiver 62B but further inhibit relative movement of the receiver 62B and fastener member 60B in the disengaging directions.

The second embodiment of the fastener 50B may be fabricated from the same kinds of materials described above for fabrication of the first embodiment of the fastener 50A. Further, a suitable instrument for applying the second embodiment of the fastener 50B may be provided to operate in the manner described above with respect to the instrument for applying the first embodiment of the fastener 50A.

THIRD EMBODIMENT OF THE FASTENER

The third embodiment of the fastener is illustrated in FIG. 6 and is designated generally therein by reference numeral 50C. The fastener 50C includes a fastening member 60C and a receiver 62C.

The fastener 50C is similar to the first and second fastener embodiments 50A and 50B, respectively, described above with reference to FIGS. 1-5. The elements of the third embodiment of the fastener 50C that are identical or functionally analogous to those of the first and second embodiments of the fasteners 50A and 50B, respectively, are designated by reference numerals identical to those used for the first and second embodiments with the exception that the third embodiment reference numerals are followed by the upper case letter C whereas the first and second embodiment reference numerals are followed by the upper case letters A and B, respectively.

The fastening member 60C includes a plurality of legs 66C which are connected together by a clamping member 68C which has a generally right rectangular parallelpiped shape.

Similarly, the receiver 62C has a generally right rectangular parallelpiped shape and defines leg receiving apertures 76C. A region around each aperture 76C may be somewhat flexible so that the receiver 62C functions in a manner identical to that of the receiver 62B described above with reference to FIG. 5.

The shape of the clamping member 68C and the shape of the receiver 62C, both being generally strip-like, may be advantageously used in those applications where it is desired to have larger areas of contact between the fastener 50C and the tissue portions.

The third embodiment of the fastener 50C may be fabricated from the same kinds of materials described above for the first and second embodiments of the fastener 50A and 50B, respectively.

The third embodiment of the fastener 50C is applied to tissue portions in a manner generally analogous to that described above for the first and second embodiments of the fastener 50A and 50B, respectively. Similarly, a suitable instrument for applying the third embodiment of the fastener 50C may be provided to operate in the manner described above with respect to the instrument for applying the first and second embodiments of the fasteners 50A and 50B, respectively.

FOURTH EMBODIMENT OF THE FASTENER

The fourth embodiment of the fastener is illustrated in FIG. 7 and is designated generally therein by reference numeral 50D. The fastener 50D includes a fastening member 60D and a receiver 62D.

The fastener 50D is similar to the third embodiment of the fastener 50C described above with reference to FIG. 6. The elements of the fourth embodiment of the fastener 50D that are identical or functionally analogous to those of the third embodiment of the fastener 50C are designated by reference numerals identical to those used for the third embodiment with the exception that the fourth embodiment reference numerals are followed by the upper case letter D whereas the third embodiment reference numerals are followed by the upper case letter C.

The fastening member 60D is similar to the fastening member 60C of the third embodiment of the fastener 50C described above with reference to FIG. 6 and has a clamping member or strip 68D from which project a plurality of spaced-apart legs 66D. The legs 66D are provided with engaging members or serrations identical to those on the legs 66C of the third embodiment of the fastener 50C.

The clamping member 68D differs, however, from the clamping member 68C of the third embodiment of the fastener in that the clamping member 68D is fabricated from a relatively flexible material. The flexible clamping member 68D is adapted to lie substantially against one of the tissue portions and to generally conform to the surface contour of the one tissue portion.

The receiver or receiver strip 62D is similarly fabricated from a relatively flexible material. It is adapted to be disposed against the other of the tissue portions opposite the fastening member 60D and to generally conform to the surface contour of the other tissue portion.

The receiver strip 62D defines means for receiving the fastening member legs 66D and means for being engaged by the engaging members (e.g., serrations) of the legs 66D after the legs have been inserted through the tissue portions. In the illustrated fourth embodiment, the leg receiving means includes apertures 76D. Serrations provided around the apertures 76D function as means for being engaged by the serrations of the fastening member legs 66D.

The fourth embodiment of the fastener 50D may be fabricated from the same kinds of materials as the first, second, and third embodiments of the fastener described hereinbefore. In addition, the fourth embodiment of the fastener 50D may be fabricated with a reduced amount of material by providing voids or regions in the fastener where no material is used.

For example, in the fastening member 60D, the clamping member or clamping strip 68D defines a plurality of apertures 96D. The apertures 96D may be square-shaped as illustrated, or may be any other suitable shape. Similarly, the receiver or receiver strip 62D may be provided with apertures 98D which may be square-shaped as illustrated or which may be any other suitable shape.

In addition, the space between each pair of fastening member legs 66D on the clamping strip 68D may define a region where one or more shorter lengths of the fastening member may be separated from the fastening member. These "separating" regions may be defined by, may be defined in, or may include voids or apertures, such as the apertures 96D.

Similarly, regions may be defined in the receiver or receiving strip 62D between the leg receiving means (e.g., leg receiving apertures 76D) where one or more shorter lengths of the receiver strip may be separated from the receiver strip. The separating regions of the receiver strip 62D may be defined by, may be defined in, or may include voids or apertures, such as the apertures 98D.

A novel method has been developed for applying the fastener 50D in a manner that uses to advantage the flexible nature of the fastener 50D. Specifically, the fastening member 60D is selected and, if it is too long for the intended application, the desired shorter length of the fastening member is separated by cutting or otherwise severing the fastening member between a selected pair of legs 66D.

Similarly, if the receiver or receiver strip 62D is too long, a shorter length of the receiver strip may be separated by cutting or severing the strip between the leg receiving means or aperture 76D.

Next, the shortened length of the fastening member 60D is disposed against one tissue portion and the shortened length of the receiver strip is disposed against the other of the tissue portions. During this step, the shortened length of the receiver strip is manipulated so as to conform to the surface contour of the tissue portion against which it is disposed.

Next, the legs of the shortened length of the fastening member 60D are inserted through the tissue portions and through the shortened length of the receiver strip 62D to conform the clamping strip 68D of the shortened length of the fastening member 60D to the surface contour of the tissue portion against which it is disposed. Insertion of the legs 66D is effected so that the legs engage the shortened length of the receiver strip 62D to prevent relative movement of the shortened length of the receiver strip 62D and of the shortened length of the fastening member 60D at least in the disengaging directions.

A suitable instrument may be provided for applying the fourth embodiment of the fastener 50D according to the above-described method.

FIFTH EMBODIMENT OF THE FASTENER

The fifth embodiment of the fastener is illustrated in FIGS. 8 and 9 and is designated generally therein by reference numeral 50E. The fastener 50E includes a fastening member 60E and a receiver 62E.

The components of fastener 50E include some basic features which are analogous to those of the first embodiment of the fastener 50A described above with reference to FIG. 1-4. The elements of the fifth embodiment of the fastener 50E that are functionally analogous to those of the first embodiment of the fastener 50A are designated by reference numerals identical to those used for the first embodiment with the exception that the fifth embodiment reference numerals are followed by the upper case letter E whereas the first embodiment reference numerals are followed by the upper case letter A.

The fastening member 60E has a generally cylindrical clamping member 68E although other shapes are suitable for the clamping member 68E. The clamping member 68E connects a plurality of spaced-apart legs 66E that have distal ends 70E (FIG. 9) adapted to penetrate the tissue portions. The elongate clamping member 68E is preferably oriented generally perpendicular to the legs 66E.

Each leg 66E defines, on its exterior along at least a portion of its length, a plurality of barbs 80E which are each angled rearwardly away from the leg distal end 70E. Preferably, each barb 80E has a generally conical configuration with a distal end portion that is relatively flexible. As best illustrated in FIGS. 8 and 9, the barbs 80E are preferably arranged in groups of four barbs at spaced longitudinal locations along the length of each leg 66E with the barbs in each group of four barbs being equally spaced about the periphery of each leg 66E.

The receiver 62E includes a flexible filament mesh 76E adapted to receive the fastening member legs 66E after the legs have been inserted through the tissue portions. The mesh 76E has a grid-like arrangement of the filaments. The mesh 76E extends across, and is secured to, a rigid peripheral frame 78E.

To apply the fastener 50E to hold together two tissue portions, the receiver 62E is disposed against one of the tissue portions (e.g., tissue portion 52 as illustrated in FIG. 9). The fastening member 60E is disposed against the other of the tissue portions (e.g., tissue portion 54 in FIG. 9) and both the receiver mesh 76E and the tissue portions are penetrated with the fastening member legs 66E. The barbs 80E engage both the mesh 76E and one tissue portion (e.g., tissue portion 52) so as to inhibit relative movement of the receiver 62E and fastening member 60E at least in the disengaging directions.

The barbs 80E are flexible enough to be bent rearwardly as the fastening member legs 66E are pushed through the tissue portions. However, the barbs 80E are resilient enough to assume their original angle after they have passed through the tissue portions. Thus, those barbs 80E which have penetrated and extend beyond the tissue portions will engage the mesh 76E and the adjacent tissue portion.

The fastener 50E may be fabricated from the same materials as the first four embodiments of the fastener described above with reference to FIGS. 1-7. Additionally, a suitable instrument for applying the fastener 50E may be provided to apply the fastener 50E to the tissue portions in accordance with the method described above.

SIXTH EMBODIMENT OF THE FASTENER

The sixth embodiment of the fastener is illustrated in FIGS. 10 and 11 wherein three identical fasteners are each designated generally by the reference numeral 50F. The elements of the sixth embodiment of the fastener 50F that are identical or functionally analogous to those of the first embodiment of the fastener 50A are designated by reference numerals identical to those used for the first embodiment with the exception that the sixth embodiment reference numerals are followed by the upper case letter F whereas the first embodiment reference numerals are followed by the upper case letter A.

The fastener 50F includes a fastening member 60F which comprises a plurality of spaced-apart legs 66F that each have a distal end 70F adapted to pass through tissue portions. The legs 66F may be connected as illustrated by a link member 68F which is generally perpendicular to the legs 66F.

Each leg 66F defines, on its exterior along at least a portion of its length, a plurality of barbs 80F which are angled rearwardly away from the leg distal end 70F. The barbs 80F may have the same general configuration and orientation as the barbs 80E of the fastener 50E described above with reference to FIGS. 8 and 9.

The fastener 50F further includes a flexible filament mesh 76F which extends outwardly from, and generally normal to, each of the legs 66F so as to define a leg receiving area. The mesh 76F may extend in a generally triangular configuration around both of the legs 66F of a fastening member 60F as illustrated. The mesh 76F may be loosely disposed on the fastening member legs 66F between the link member 68F and the leg distal ends 70A as illustrated. Preferably, the mesh 76F is adjacent the link member 68F and may even be in contact with the link member 68F. Preferably, there is also a generally rigid frame 78F around the periphery of the mesh 76F, and the mesh 76F is secured to the frame 78F.

The mesh 76F and its frame 78F may be loosely disposed on the legs 66F adjacent the link member 68F. The mesh 76F and frame 78F need not be immovably secured or fixed to the legs 66F or to the link member 68F.

The fasteners 50F may be fabricated from the same materials as the first through the fifth embodiments of the fastener described above with reference to FIG. 1-9.

The fasteners 50F are applied to tissue portions in a novel manner to hold together the tissue portions. Specifically, at least a first fastening member 60F and the associated mesh 76F are disposed against one of the tissue portions and the tissue portions are penetrated by the legs 66F of the fastening member 60F.

A second fastening member 60F and associated mesh 76F are disposed against the other of the tissue portions. The fastening member legs 66F of the second fastening member 60F are inserted through the tissue portions so as to penetrate both tissue portions. The locations of the leg penetrations of both the first and second fastening members 60F are selected so that at least one leg of each fastening member penetrates the mesh around a leg of the other fastening member and so that the barbs of at least one leg of each fastening member engage both the mesh of the other fastening member and one of the tissue portions so as to inhibit relative movement of the fastening members in at least the disengaging directions.

In FIG. 11, three identical fasteners 50F are shown holding together the two tissue portions 54 and 52. The fastener 50F that is shown inserted from the bottom below tissue portion 52 has its associated mesh penetrated by a leg of each of the other two fasteners 50F which have been inserted from the top over tissue portion 54. Each of these upper fasteners 50F is engaged by one of the two legs of the lower fastener 50F. With reference to FIG. 10, it can be seen that the triangular shape of the mesh 76F provides a region defined in a vertex (opposite the link member 68F) which can receive an engaging leg of another fastener 50F.

A suitable instrument may be used for applying the fasteners 50F to hold together the tissue portions according to the method described above.

SEVENTH EMBODIMENT OF THE FASTENER

A seventh embodiment of the fastener is illustrated in FIG. 12 where it is designated generally by the reference numeral 50G. Three such fasteners 50G are shown in a typical orientation wherein they would be applied to tissue portions. Each fastener 50G is similar, and functions in an analogous manner, to the sixth embodiment of the fastener 50F described above with reference to FIGS. 10 and 11. The elements of the seventh embodiment of the fastener 50G that are identical or functionally analogous to those of the sixth embodiment of the fastener 50F are designated by reference numerals identical to those used for the sixth embodiment with the exception that the seventh embodiment reference numerals are followed by the upper case letter G whereas the sixth embodiment reference numerals are followed the upper case letter F.

Each fastener 50G includes two spaced-apart legs 66G that each have a distal end 70G adapted to pass through the tissue portions. Preferably, the legs 66G are connected by a link member 68G. The legs 66G have barbs 80G which may be identical to the barbs 80F of the sixth embodiment of the fastener 50F described above.

Rather than have a single mesh extending around both legs 66G, the fastener 50G includes two separate portions of flexible filament mesh 76G --one of the portions having a generally circular configuration around one of the fastening member legs 66G and the other of the portions having a generally circular configuration around the other of the fastening member legs 66G. Each portion of mesh 76G may include a generally rigid frame 78G. Each portion of mesh 76G may be loosely disposed on a leg 66G adjacent the link member 68G. A fixed securement of each mesh portion to the fastener 50G is not required.

The fasteners 50G may be applied to the tissue portions in a manner generally similar and analogous to that used in applying the sixth embodiment of the fasteners 50F described above with reference to FIGS. 10 and 11.

The fasteners 50G may be fabricated from the same materials as the first through the sixth embodiments of the fasteners described hereinbefore.

FASTENER ADJUSTABILITY

With each of the fastener embodiments described above, it is seen that the fastener can accommodate various thicknesses of tissue. The fasteners may be inserted into the tissue and relative movement may be effected until the desired tissue compression is achieved. The fastener components lock together at any of a plurality of closely spaced points along the length of the fastening member legs so that a wide range of adjustability is conveniently provided.

ALTERNATIVE DESIGN FEATURES

In the embodiments shown in FIGS. 1-6 and 8, the legs of each fastening member are connected by a portion of the fastening member (e.g., the link or clamping member) which is illustrated as being generally straight and extending perpendicular to the legs. The structure need not be limited to such a shape however. Instead, all or a portion of the length of the fastening member between any two adjacent legs may be arched or arcuate or may include an arcuate portion (e.g., an inverted U-shaped configuration). This would function to initially provide a free space between the upper tissue portion and the top of the fastening member to allow for some expansion of the tissue.

However, in those situations where increased initial tissue compression is desired, a modified receiver structure may be provided to cooperate with the above-described arcuate fastening member. Specifically, the receiver need not have a flat upper surface as illustrated. Rather, the upper surface of the receiver may be arcuate (e.g., convex) so as to generally match or correspond with the arcuate shape of the fastening member. This can result in an increased compression of the two tissue portions between the receiver and fastening member.

From the foregoing, it will be observed that numerous variations and modifications may be effected without departing from the true spirit and scope of the novel concept of the invention. It is to be understood that no limitation with respect to the specific articles, instruments, and methods illustrated herein is intended or should be inferred. It is, of course, intended to cover by the appended claims all such modifications as fall within the scope of the claims.

What is claimed is:

1. A fastener adapted to hold together, in conjunction with one or more other similar fasteners, two portions of mammalian tissue, such as are defined by a wound or incision, to facilitate healing of the wound or incision, said fastener comprising:

a fastening member with at least two spaced-apart legs each having a distal end adapted to pass through the tissue portions, each said leg defining on its exterior along at least a portion of its length a plurality of barbs angled rearwardly away from the leg distal end; and a mesh of flexible filaments, said mesh having a generally triangular configuration, said mesh extending between adjacent legs and said mesh extending outwardly from, and generally normal to, each of said legs to define a leg receiving area whereby the legs of one of the fastening members may be passed through the tissue portions from one side of said wound or incision with the mesh being disposed against one of said tissue portions and whereby the legs of another of the fastening members may be inserted through the tissue portions from the other side of said wound or incision with the mesh of said other fastening member lying substantially against the other of said tissue portions so that at least one leg of each of said fastening members penetrates the mesh of the other fastening member with the leg barbs engaging both the mesh and the adjacent tissue portions so as to inhibit relative movement of said fastening members at least in the disengaging directions.

2. A fastener adapted to hold together, in conjunction with one or more other similar fasteners, two portions of mammalian tissue, such as are defined by a wound or incision, to facilitate healing of the wound or incision, said fastener comprising:

a fastening member with at least two spaced-apart legs each having a distal end adapted to pass through the tissue portions, each said leg defining on its exterior along at least a portion of its length a plurality of barbs angled rearwardly away from the leg distal end; and each of said legs having a mesh of flexible filaments extending around said leg, said mesh having a generally circular configuration, said mesh extending outwardly from, and generaly normal to said leg to define a leg receiving area whereby the legs of one of the fastening members may be passed through the tissue portions from one side of said wound or incision with the mesh being disposed against one of said tissue portions and whereby the legs of another of the fastening members may be inserted through the tissue portions from the other side of said wound or incision with the mesh of said other fastening member lying substantially against the other of said tissue portions so that at least one leg of each of said fastening members penetrates the mesh of the other fastening member with the leg barbs engaging both the mesh and the adjacent tissue portions so as to inhibit relative movement of said fastening members at least in the disengaging directions.

* * * * *